United States Patent [19]

Childs

[11] 4,172,851
[45] Oct. 30, 1979

[54] PERFLUOROALKYL ALKYL KETONES FROM ALKANOIC AND PERFLUOROALKANOIC ANHYDRIDES

[75] Inventor: William V. Childs, Bartlesville, Okla.

[73] Assignee: Phillips Petroleum Company, Bartlesville, Okla.

[21] Appl. No.: 856,480

[22] Filed: Dec. 1, 1977

[51] Int. Cl.$^2$ ............................................. C07C 45/00
[52] U.S. Cl. ............................ 260/593 H; 260/593 R
[58] Field of Search ................ 260/593 H, 595, 593 R

[56] References Cited

U.S. PATENT DOCUMENTS 3,468,956   9/1969   Mead .................................... 260/595

OTHER PUBLICATIONS

House, Modern Synthetic Reactions, 2nd Ed. (1973), p. 734.
Smith et al., J.A.C.S., vol. 84, pp. 4285–4288 (1962).
Yakerson et al., Chem. Abst., vol. 74, p. 316, #41920w, (Brit. Pat. 1208802), (1971).

Primary Examiner—James H. Reamer

[57] ABSTRACT

Perfluoroalkyl alkyl ketones are prepared by reaction of a perfluoroalkanoic acid anhydride and a non-fluorinated alkanoic acid anhydride.

8 Claims, No Drawings

PERFLUOROALKYL ALKYL KETONES FROM ALKANOIC AND PERFLUOROALKANOIC ANHYDRIDES

In one of its aspects, this invention relates to the preparation of partially fluorinated ketones.

In one of its concepts, the invention provides a process for the preparation of a perfluoroalkyl alkyl ketone by reaction of an anhydride of a perfluoroalkanoic acid and an anhydride of a nonfluorinated alkanoic acid.

In another of its concepts, the invention provides a reaction of two dissimilar anhydrides with a loss of carbon dioxide at a temperature in the approximate range of ambient room temperature and a temperature suitable to enable refluxing, without formation of substantial amounts of decomposition or undesirable products.

Perfluoroalkyl alkyl ketones are useful intermediates that can be readily converted by chemical means such as electrochemical fluorination to polyfluorinated dialkyl ketones. Nonfluorinated dialkyl ketones are more difficult to convert to polyfluorinated dialkyl ketones by the same process and thereby less desirable as a fluorination feedstock. The carbonyl or ketone group of these subsequent polyfluorinated dialkyl ketones are highly reactive and as such lead to further preparations of specialty type chemicals that have various industrial applications. For example, polyacrylates and polyethers derived from hexafluoroacetone, a typical polyfluorinated dialkyl ketone, can be used to make oil (antistain) and water (antiwetting) repellent coatings for textiles. The hydrates of these polyfluorinated dialkyl ketones are powerful solvents for acetal resins, polyamides, polyvinyl alcohol, polyesters and natural products containing active groups such as amides, amines, esters, alcohols or ketones. Other derivatives of the polyfluorinated dialkyl ketones perpared via the perfluoroalkyl alkyl ketones of the current invention can be used for solvents, heat transfer agents, pesticides and interneuronal depressants of the central nervous system.

It is an object of this invention to prepare a ketone. It is another object of this invention to prepare a perfluoroalkyl alkyl ketone. It is another object of this invention to provide a process for the preparation of a perfluoroalkyl alkyl ketone. A further object of the invention is to prepare 1,1,1,2,2,3,3-heptafluoro-4-heptanone. It is a further object still of the invention to bring together and cause to react two dissimilar anhydrides of an alkanoic acid, e.g., of perfluoroalkanoic acid and a nonfluorinated alkanoic acid, e.g., of heptafluorobutyric acid and butyric acid.

Other aspects, concepts, objects and the several advantages of the invention are apparent from the study of this disclosure and the appended claims.

According to the present invention, there is provided the preparation of a partially fluorinated alkyl ketone, i.e., perfluoroalkyl alkyl ketone which can be represented by the formula

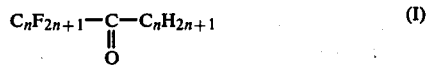

wherein n can vary from 1 to 10.

Further according to the invention, the said ketones are prepared by a reaction of an anhydride of a perfluoroalkanoic acid and the anhydride of a nonfluorinated alkanoic acid.

In view of the product which is obtained the synthesis appears to proceed by a simple adduct formed by the two dissimilar anhydrides with a loss of carbon dioxide from the said adduct, according to equations which follow:

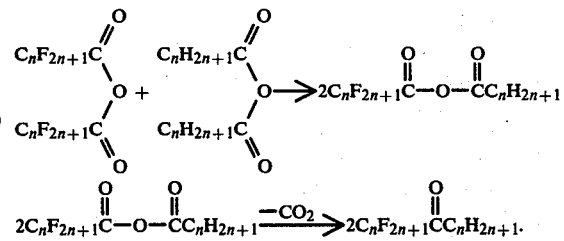

The nonfluorinated acid anhydrides useful in this invention include anhydrides of $C_2$-$C_{11}$ carboxylic acids such as acetic, propionic, butyric, valeric, caproic, enanthic, caprylic, pelargonic, decanoic, and undecanoic. Mixed anhydrides of these nonfluorinated acids can also be used. The coreactants are the perfluorinated acid anhydrides of the aforementioned nonfluorinated acid anhydrides except that all of the hydrogen atoms are replaced with fluorine atoms. Typical examples of these materials are trifluoroacetic anhydride, pentafluoropropionic anhydride, heptafluorobutyric anhydride, and the like. Typical products which would result from these mixed anhydrides are:

| Alkanoic Anhydride | Perfluoroalkanoic Anhydride | Product |
|---|---|---|
| Acetic | Trifluoroacetic | 1,1,1-Trifluoro-2-propanone |
| Propionic | Trifluoroacetic | 1,1,1-Trifluoro-2-butanone |
| Butyric | Trifluoroacetic | 1,1,1-Trifluoro-2-pentanone |
| Valeric | Trifluoroacetic | 1,1,1-Trifluoro-2-hexanone |
| Caproic | Trifluoroacetic | 1,11-Trifluoro-2-heptanone |
| Acetic | Pentafluoropropionic | 1,1,1,2,2-Pentafluoro-3-butanone |
| Propionic | Pentafluoropropionic | 1,1,1,2,2-Pentafluoro-3-pentanone |
| Butyric | Pentafluoropropionic | 1,1,1,2,2-Pentafluoro-3-hexanone |
| Valeric | Pentafluoropropionic | 1,1,1,2,2-Pentafluoro-3-heptanone |
| Caproic | Pentafluoropropionic | 1,1,1,2,2-Pentafluoro-3-octanone |
| Acetic | Heptafluorobutyric | 1,1,1,2,2,3,3-Heptafluoro--pentanone |
| Propionic | Heptafluorobutyric | 1,1,1,2,2,3,3-Heptafluoro-4-hexanone |
| Butyric | Heptafluorobutyric | 1,1,1,2,2,3,3-Heptafluoro-4-heptanone |
| Valeric | Heptafluorobutyric | 1,1,1,2,2,3,3-Heptafluoro-4-octanone |
| Caprioc | Heptafluorobutyric | 1,1,1,2,2,3,3-Heptafluoro-4-nonanone |

The current invention is not limited to the above reaction products which are only listed to illustrate the type of products produced. Both the alkanoic and perfluoroalkanoic anhydrides can be branched to give the corresponding branched products. Mixtures of more than two reactants can be made.

The reaction is preferred to be conducted in the absence of a solvent although solvents can be used if the separation of the solvent and product can be easily achieved. Such solvents would, of course, have to be inert under the conditions of the reaction since the activity of the carbonyl grouping is high even though the product is not fully flourinated.

The reaction can be conducted without a catalyst in a 1-to-1 mole ratio of the two dissimilar anhydrides although an excess of either anhydride would work easily as well.

The reaction is preferred to be conducted in glass between ambient room temperature and a temperature suitable to enable refluxing yet not so high as to produce undesirable decomposition products. The reaction takes place at atmospheric pressure; the pressure does not appear to be critical. An inert gas can be used for ebullition to assist in product separation which can be made by simple distillation. Other appropriate separation methods such as extraction, adsorption, crystallization, etc., can also be used.

The reaction time will vary depending on temperature, pressure, and type of anhydride employed. Under normal conditions, a reaction time of 1 to 24 hours, preferably 4–12 hours, is considered satisfactory.

The reaction can be carried out either batchwise or continuously using any suitable mode or order of addition. Since the reaction is generally exothermic, it may be convenient to slowly add one anhydride to a refluxing quantity of the other anhydride. Although the reaction will proceed upon merely contacting the reactants, it is now preferred to heat at least one of them moderately, say, to reflux temperature.

The following example serves to typify the reaction of the current invention.

EXAMPLE

To a five liter glass flask fitted with a heating mantle, mechanical stirrer, thermometer, nitrogen ebullator and condenser was added 216 grams (0.526 moles) of heptafluorobutyric anhydride. The liquid contents were heated to reflux (110° C.) with stirring whereupon 52.4 grams (0.331 moles) of butyric anhydride was slowly added at a rate of about 1 drop per second. After about 2.5 hours, the addition, which was exothermic, was completed, the final temperature being about 138° C. An amber colored mixture was obtained. It was subjected to a simple distillation using a Snyder-type distillation column. The product, 1,1,1,2,2,3,3-heptafluoro-4-heptanone, codistilled with heptafluorobutyric anhydride between 105° C. and 116° C. Fractions were collected between these temperatures and the amount of product present in each fraction was determined by using a 426 cm (14 ft.)×0.31 cm (0.125 in.) gas chromatographic column packed with Propak PS (Waters Associates Trademark) and operated isothermally at 200° C. with a helium gas flow rate of 4 cc/min. There was obtained 149.4 grams of distillate containing 16.26 weight percent 1,1,1,2,2,3,3-heptafluoro-4-heptanone, confirmed by mass spectrometer study. The yield was calculated as follows:

$$\frac{149.4 \text{ grams} \times 16.26\%}{240.11 \text{ (Mol. wt. of product)}} = 0.101 \text{ moles of product}$$

$$\frac{0.5 \text{ conversion factor} \times 0.101 \text{ moles of product} \times 100}{0.331 \text{ moles of butyric anhydride}} = 15.26 \text{ mole percent yield.}$$

Reasonable variations and modifications are possible within the scope of the foregoing disclosure and the appended claims to the invention the essence of which is that a perfluoroalkyl alkyl ketone, as described, is prepared by reaction of an anydride of a perfluoroalkanoic acid and the anhydride of a nonfluorinated alkanoic acid.

What is claimed is:

1. The preparation of a partially fluorinated ketone which comprises bringing together under reaction conditions including from about room temperature to a temperature suitable to enable refluxing yet not so high as to produce undesirable decomposition products an anhydride of a perfluoroalkanoic acid and an anhydride of a nonfluorinated alkanoic acid.

2. The preparation of claim 1 wherein the first anhydride is heptafluorobutyric anhydride and the second is butyric anhydride.

3. The preparation of claim 1 wherein the reaction conditions include a moderate heating of at least one of the reactants.

4. The preparation of claim 2 wherein the reaction conditions include a moderate heating of at least one of the reactants.

5. According to claim 4 wherein at least one of the reactants is heated to reflux and the remaining reactant is added to the refluxing reactant.

6. A preparation according to claim 1 wherein the partially fluorinated ketone can be represented by the formula

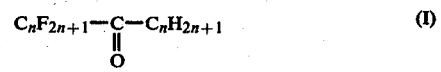

wherein n can vary from 1 to 10 and wherein said ketone is formed according to reactions which can be represented by the following equations:

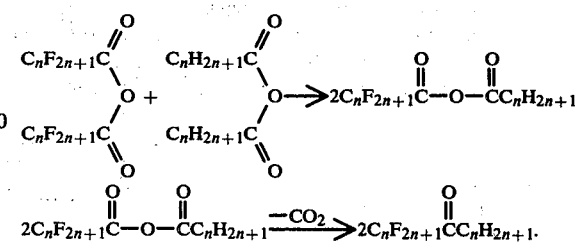

7. A preparation according to claim 6 wherein the nonfluorinated acid anhydrides are selected from the anhydrides of $C_2$–$C_{11}$ carboxylic acids such as acetic, propionic, butyric, valeric, caproic-enanthic, caprylic, pelargonic, decanoic, and undecanoic acids and the mixed anhydrides of these acids and the reactants are the perfluorinated acid anhydrides of the aforementioned nonfluorinated acid anhydrides with all of the hydrogen atoms replaced with fluorine atoms.

8. A preparation according to claim 1, wherein the reaction is of heptafluorobutyric anhydride and butyric anhydride.

* * * * *